United States Patent
Song et al.

(10) Patent No.: US 8,926,523 B2
(45) Date of Patent: Jan. 6, 2015

(54) METHOD AND APPARATUS FOR CARDIAC FUNCTION MONITORING

(71) Applicant: Medtronic, Inc., Minneapolis, MN (US)

(72) Inventors: Zhendong Song, Medina, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/794,898

(22) Filed: Mar. 12, 2013

(65) Prior Publication Data

US 2013/0289430 A1  Oct. 31, 2013

Related U.S. Application Data

(60) Provisional application No. 61/639,234, filed on Apr. 27, 2012.

(51) Int. Cl.
| | | |
|---|---|---|
| *A61B 5/02* | (2006.01) | |
| *A61N 1/00* | (2006.01) | |
| *A61B 5/0215* | (2006.01) | |
| *A61N 1/365* | (2006.01) | |
| *A61B 5/0245* | (2006.01) | |
| *A61N 1/362* | (2006.01) | |
| *A61B 7/04* | (2006.01) | |
| *A61N 1/05* | (2006.01) | |

(52) U.S. Cl.
CPC . *A61B 7/04* (2013.01); *A61N 1/056* (2013.01); *A61B 5/02158* (2013.01); *A61N 1/36578* (2013.01); *A61N 1/36585* (2013.01); *A61B 5/0245* (2013.01); *A61N 1/36564* (2013.01); *A61N 1/362* (2013.01)
USPC .............................................. 600/528; 607/6

(58) Field of Classification Search
CPC ............. A61B 5/0245; A61B 5/02158; A61B 5/0205; A61N 1/362; A61N 1/36578; A61N 1/36564
USPC ................................................ 600/528; 607/6
See application file for complete search history.

(56) References Cited

U.S. PATENT DOCUMENTS

| | | | |
|---|---|---|---|
| 4,672,976 A | 6/1987 | Kroll | |
| 5,168,869 A | 12/1992 | Chirife | |
| 5,715,827 A * | 2/1998 | Corl et al. ..................... 600/486 |
| 6,418,346 B1 | 7/2002 | Nelson | |
| 6,442,433 B1 | 8/2002 | Linberg | |
| 6,480,745 B2 | 11/2002 | Nelson | |
| 6,599,250 B2 | 7/2003 | Webb | |
| 6,650,940 B1 * | 11/2003 | Zhu et al. ......................... 607/28 |
| 6,869,404 B2 | 3/2005 | Schulhauser | |
| 6,885,889 B2 | 4/2005 | Chinchoy | |
| 6,937,899 B2 | 8/2005 | Sheldon | |

(Continued)

*Primary Examiner* — Catherine Voorhees
(74) *Attorney, Agent, or Firm* — Michael C. Soldner

(57) ABSTRACT

An implantable medical device that includes a first elongated lead body having an outer surface and an opening along the outer surface, a sensor positioned along the lead body and configured to receive acoustic signals through the opening of the first lead body and generate an electrical signal representative of sounds produced at a targeted location along a patient's cardiovascular system. A therapy delivery module is capable of delivering a cardiac therapy via predetermined electrodes of a plurality of electrodes, and a processor is configured to detect a cardiac event in response to the sensed cardiac electrical signals, determine a plurality of time intervals between the electrical signals and acoustic signals, determine a correlation between the electrical signals and the acoustic signals, and control the therapy delivery module to deliver therapy in response to the determined correlation.

20 Claims, 12 Drawing Sheets

(56) References Cited

U.S. PATENT DOCUMENTS

| | | |
|---|---|---|
| 7,052,466 B2 | 5/2006 | Scheiner |
| 7,203,541 B2 | 4/2007 | Sowelam |
| 7,509,169 B2 | 3/2009 | Eigler |
| 7,844,331 B2 * | 11/2010 | Li et al. .................... 607/14 |
| 7,914,452 B2 | 3/2011 | Hartley |
| 7,998,091 B2 | 8/2011 | Carim |
| 8,118,751 B2 * | 2/2012 | Dobak, III ................ 600/528 |
| 2004/0230129 A1 * | 11/2004 | Haefner ..................... 600/510 |
| 2004/0254483 A1 * | 12/2004 | Zdeblick et al. ........... 600/486 |
| 2006/0270939 A1 | 11/2006 | Wariar |
| 2007/0129765 A1 * | 6/2007 | Gilkerson et al. ............ 607/18 |
| 2007/0142866 A1 | 6/2007 | Li |
| 2007/0162080 A1 | 7/2007 | Brockway |
| 2007/0282397 A1 | 12/2007 | Ball |
| 2008/0039733 A1 | 2/2008 | Unver |
| 2010/0010358 A1 | 1/2010 | Boute |
| 2010/0262206 A1 | 10/2010 | Zdeblick |
| 2010/0331903 A1 | 12/2010 | Zhang |
| 2011/0015702 A1 * | 1/2011 | Ternes et al. ................ 607/62 |
| 2011/0105932 A1 | 5/2011 | Bauer |

* cited by examiner

METHOD AND APPARATUS FOR CARDIAC FUNCTION MONITORING

RELATED APPLICATION

The present application claims priority and other benefits from U.S. Provisional Patent Application Ser. No. 61/639,234, filed Apr. 27, 2012, entitled "METHOD AND APPARATUS FOR CARDIAC FUNCTION MONITORING", incorporated herein by reference in its entirety.

FIELD OF THE DISCLOSURE

The disclosure relates generally to medical devices and, in particular, to a heart sound recording apparatus and method for monitoring cardiac function.

BACKGROUND

Heart sounds contain a great deal of diagnostic information. A stethoscope is a standard instrument used in clinical examinations and has aided in enabling clinicians to become familiar with normal and abnormal heart and lung sounds. Clinicians typically refer to four heart sounds, S1, S2, S3 and S4. The first heart sound, S1, corresponds to the start of ventricular systole and is generated by the abrupt closure of the mitral and tricuspid valves between the ventricles and atria as ventricular pressure exceeds atrial pressure. The second heart sound, S2, is generated by the closure of the aortic and pulmonary valves, near the end of ventricular systole and start of ventricular diastole.

The third heart sound, S3, is associated with early, passive diastolic filling of the ventricles, and the fourth heart sound, S4, is associated with late, active filling of the ventricles due to atrial contraction. The third sound is generally difficult to hear in a normal patient using a stethoscope, and the fourth sound is generally not heard in a normal patient. Presence of the third and fourth heart sounds may indicate a pathological condition.

Implementation of acoustical sensors in implantable medical devices such as cardiac pacemakers has been proposed because of the valuable information that can be obtained relating to the occurrence of the standard heart sounds S1, S2, S3 and S4 (if present). In addition to the standard S1 through S4 heart sounds, a large amount of acoustical information correlated to blood flow through the heart chambers, valves and arteries could potentially be gleaned from an implantable acoustical sensor. However, even when implanted, an acoustical sensor positioned to sense cardiac sounds will be subjected to lung and other physiological sounds and non-physiological noise. For example, heart sound sensing using a piezoelectric transducer positioned in the pacemaker housing will be somewhat hampered due to filtering of high frequency cardiac sounds by the lungs and the influence of respiration on the acoustical signal. A need remains, therefore, for an implantable acoustical sensor useful for monitoring cardiac sounds with high specificity and sensitivity.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
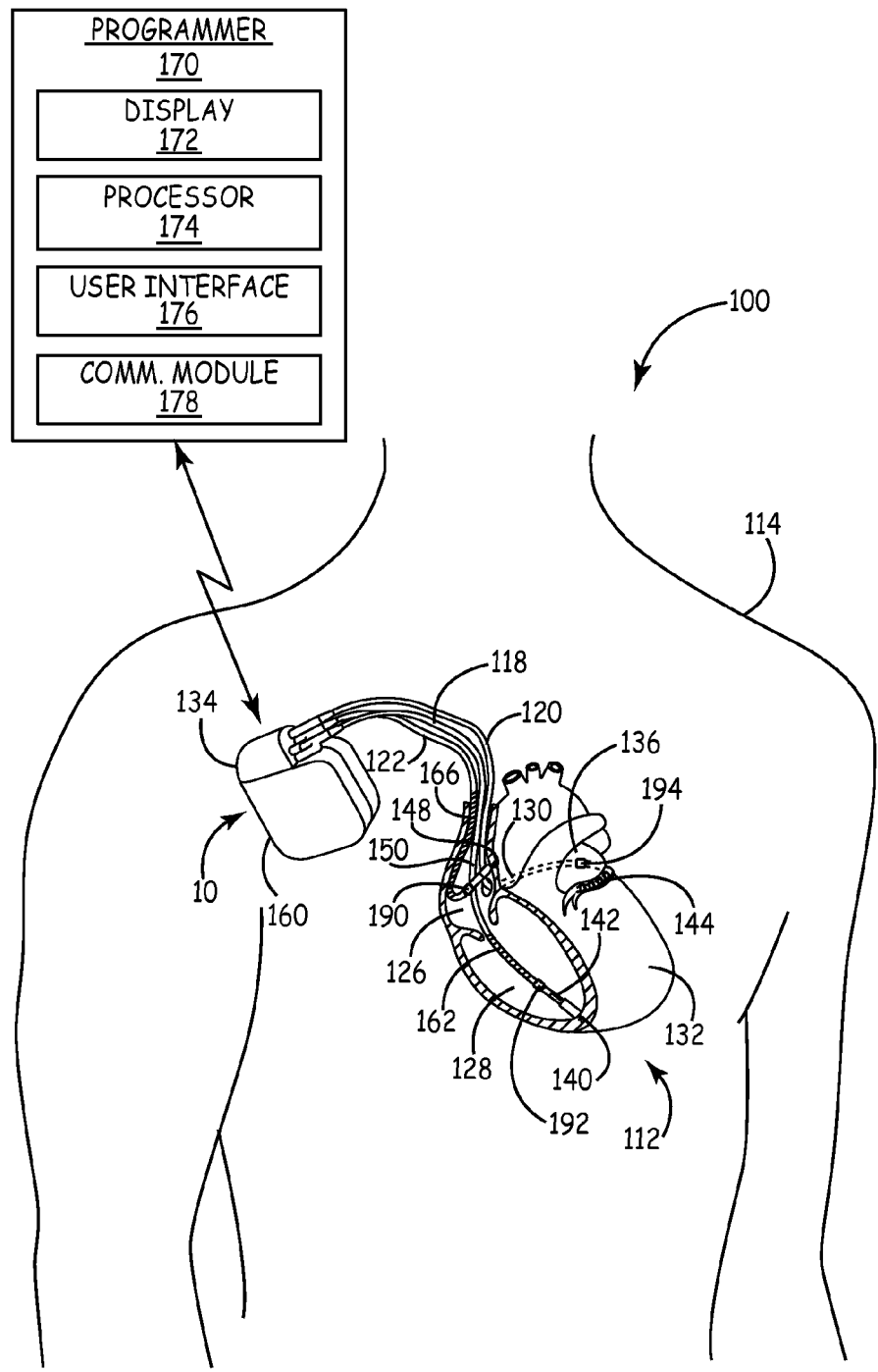
FIG. 1 is a functional block diagram of an IMD system for acquiring acoustical signals for monitoring cardiac function.

FIG. 1 is a functional block diagram of an IMD system 100 for acquiring acoustical signals for monitoring cardiac function. System 100 includes IMD 10 coupled to leads 118, 120, and 122 which carry multiple electrodes for sensing cardiac EGM signals and/or delivering cardiac pacing pulses. IMD 10 is configured for bidirectional communication with programmer 170. IMD 10 may be, for example, an implantable pacemaker, cardiovertor, and/or defibrillator that provides electrical signals to heart 112 via electrodes coupled to one or more of leads 118, 120, and 122.

Each of leads 118, 120 and 122 is shown carrying a hydrophone 190, 192, and 194 for use in sensing cardiac function as will be described in greater detail below. The hydrophones 190, 192, and 194 are adapted for positioning directly in the blood stream and are deployed to a desired sensing location for monitoring specific cardiac or blood flow sounds at selected frequencies to obtain acoustical signals correlated to cardiac or hemodynamic function.

The hydrophones 190, 192, and 194 are configured to receive acoustical signals through an opening in the lead body of the respective leads 118, 120 and 122 and generate an electrical signal representative of sounds produced at a targeted location along a patient's cardiovascular system. An outer surface of the elongated lead body of each of leads 118, 120 and 122 may include a shaped contour for directing the opening in the lead body for receiving the sounds from a direction of the targeted location. A shaped contour of the outer surface of the lead body may include a pre-shaped curve or bend of the lead body, a recessed surface, or a convex or spherical surface.

The opening may extend along the shaped contour, i.e. along a pre-shaped curve, and/or along a recessed surface or along a convex surface. The opening may alternatively extend along the outer surface of the lead body proximally or distally to a pre-shaped curve for directing the opening toward a targeted cardiovascular location for receiving sounds generated at the targeted location. The lead body opening and associated hydrophone receiving sound signals through the opening may be positioned along an outer side surface of the lead body as generally shown in FIG. 1. Alternatively or additionally, an opening and associated hydrophone may be positioned along an outer surface of the distal tip of the lead body.

The hydrophone and the lead body may be hermetically sealed to prevent influx of body fluids into the lead body and into the hydrophone. Various embodiments of a lead carrying a hydrophone and having an outer surface including a shaped contour for directing an opening toward a targeted sound source to enable directional sensing of cardiovascular sounds by a hydrophone will be further described in detail in conjunction with FIGS. 3A through 4C.

IMD 10 is shown configured for multi-chamber pacing and sensing in the right atrium (RA) 126, the right ventricle (RV) 128, and the left ventricle (LV) 132 using leads 118, 120 and 122. The system shown is configured for delivering cardiac resynchronization therapy (CRT) for treating heart failure in patient 114 according to one embodiment. IMD 10 may additionally or alternatively be configured for detecting cardiac arrhythmias and delivering arrhythmia therapies, such as anti-tachycardia pacing therapy and cardioversion/defibrillation shocks. IMD 10 is one example of numerous types of devices that an acoustical signal sensing system and associated methods for monitoring cardiac conditions as described herein may be implemented. Such devices may be capable of delivering a therapy including one or more of cardiac pacing, neurostimulation, or fluid delivery for administering a pharmacological agent or biological fluid.

In other embodiments, an IMD system including acoustical signal monitoring may be provided as a monitoring-only system which acquires and analyzes acoustical signals for diagnostic and prognostic purposes without having therapy delivery capabilities. Furthermore, a device for performing the methods described herein is not limited to fully implantable medical devices but may be implemented using external components coupled to implantable leads or catheters carrying at least one hydrophone positioned in the blood stream and thus may include a combination of implantable and external components. As such, the system 100 shown in FIG. 1 is one illustrative embodiment of a system in which a hydrophone and associated methods described herein may be implemented.

IMD 10 delivers RV pacing pulses and senses RV intracardiac EGM signals using RV tip electrode 140 and ring electrode 142 positioned in the RV 128. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the right atrium (RA) 126 and into a cardiac vein 130 via the coronary sinus. In some embodiments, coronary sinus lead 120 may include electrodes positioned along the left atrium (LA) 136 for sensing left atrial EGM signals and deliver LA pacing pulses.

IMD 10 senses RA EGM signals and delivers RA pacing pulses using RA lead 122, carrying tip electrode 148 and ring electrode 150. RA lead 122 is shown carrying a coil electrode 166 which may be positioned along the superior vena cava (SVC) for use in delivering cardioversion/defibrillation shocks. In other embodiments, RV lead 118 carries both the RV coil electrode 162 and the SVC coil electrode 166. While IMD 10 is shown in a right pectoral implant position in FIG. 1, a more typical implant position, particularly when IMD 10 is embodied as an ICD, may be a left pectoral implant position.

IMD 10 includes internal circuitry for performing the functions attributed to IMD 10 and a housing 160 encloses the internal circuitry. It is recognized that the housing 160 or portions thereof may be configured as an active electrode for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 may provide acoustical signal data to programmer 170 via wireless telemetry. Acoustical signal data and/or an alarm or alert relating to a detected cardiac condition may be transmitted to programmer 170 for display or further transmission to a user via a communication network. Acoustical signal monitoring procedures may be performed automatically by IMD 10 according to a monitoring protocol or upon a user request using programmer 170. A patient or physician alert and/or therapy adjustments may be made automatically by IMD 10 in response to acoustical signal analysis. Alternatively, acoustical signals may be obtained by IMD 10 and transmitted to programmer 170 for analysis and display of results to a user.

Programmer 170 includes a display 172, a processor 174, a user interface 176, and a communication module 178 including wireless telemetry circuitry for communication with IMD 10. In some examples, programmer 170 may be a handheld device or a microprocessor based home monitor or clinical programming device. A user, such as a physician, technician, nurse or other clinician, may interact with programmer 170 to communicate with IMD 10. For example, the user may interact with programmer 170 via user interface 176 to retrieve physiological or diagnostic information from IMD 10. A user may also interact with programmer 170 to program IMD 10, e.g., select values for operational parameters of the IMD. A user interacting with programmer 170 may request IMD 10 to perform an acoustical signal analysis algorithm or request data stored by IMD 10 relating to acoustical signals. Processor 174 receives data from IMD 10 for use in generating a display presented on display 172 including information relating to acoustical data and any notifications or alert messages.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS. In some examples, programmer 170 may include a programming head that is placed proximate the IMD 10 to establish and maintain a communication link, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of the patient 114 using the acoustical signal monitoring described herein. Remote patient management systems may be configured to utilize the presently disclosed techniques to enable a clinician to review data derived from acoustical signals and authorize programming of IMD control parameters. For example, acoustical signals or parameters derived from the signals may be transferred from programmer 170 to a clinic or other expert center for review. The clinician or other expert may then authorize programming of the IMD for delivering or adjusting a therapy via a communications network and programmer 170. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming.

Figure 2:
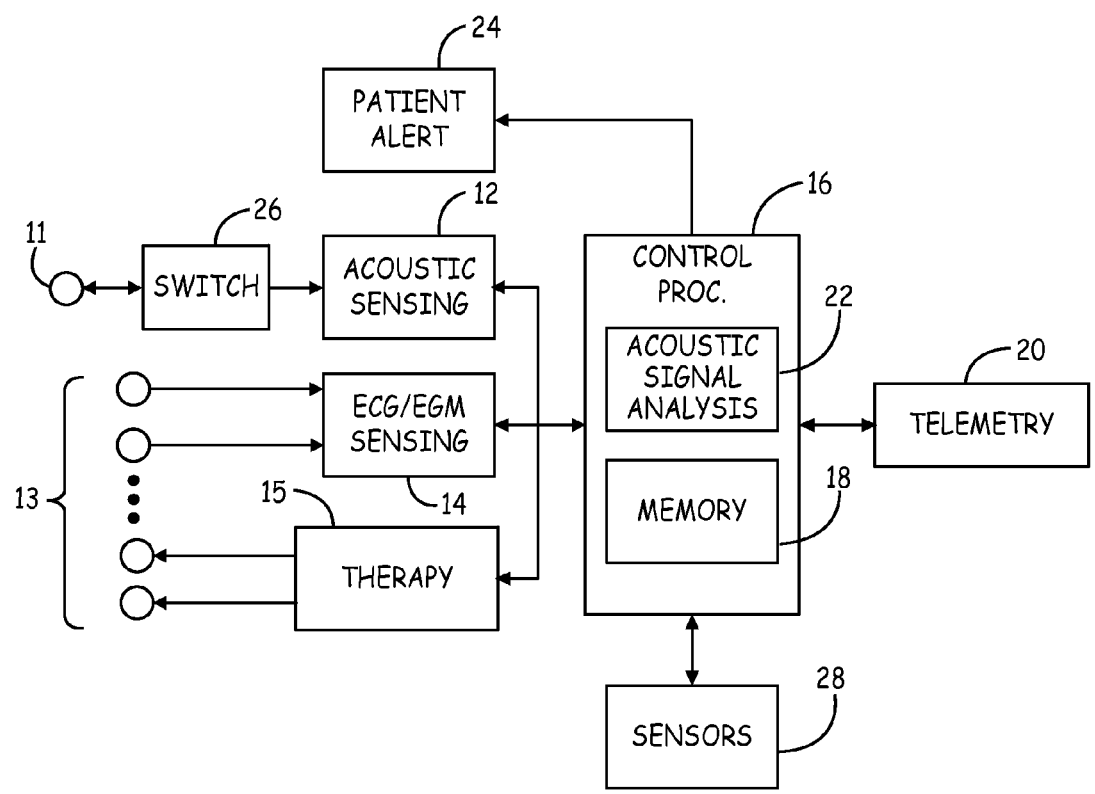
FIG. 2 is a functional block diagram of the IMD shown in FIG. 1.

FIG. 2 is a functional block diagram of IMD 10 shown in FIG. 1. IMD 10 includes an acoustical sensing module 12 coupled to one or more acoustical sensors 11, cardiac EGM signal sensing circuitry 14 and therapy delivery module 15 both coupled to electrodes 13, control processor 16 and associated memory 18, and telemetry circuitry 20. Acoustical sensing module 12 receives signals from acoustical sensors 11 for sensing acoustical signals which are provided to control processor 16.

Acoustical sensing module 12 is configured to receive signals from sensors 11 embodied as hydrophones for sensing acoustical signals from one or more targeted locations in the heart or blood vessels. For example, acoustical sensing module 12 may include multiple "channels" configured to particularly sense specific cardiac sounds based on sensing location and/or frequency. EGM sensing circuitry 14 may be used by control processor 16 to set sensing windows used by acoustical sensing module 12 for sensing acoustical signals during the cardiac cycle. Acoustical sensing module 12 may include one or more sense amplifiers, filters and rectifiers for optimizing a signal-to-noise ratio and obtaining acoustical signals useful for deriving parameters used for monitoring cardiovascular function. Separate and unique amplification and filtering properties may be provided for sensing different acoustical signal channels to improve signal quality as needed.

Acoustical sensors 11 are implemented as hydrophones which are positioned transvenously, within a vein, artery or heart chamber and may correspond to the sensors 190, 192, and 194 shown in FIG. 1, or any other hydrophones shown herein. In various embodiments, one or more leads positioned in a patient's blood stream may carry one or more sensors as will be further described herein.

When multiple acoustical sensors are implemented in an IMD system, switching circuitry 26 may be used to control which acoustical sensors, or which transducers within a sensor, are coupled to sensing module 12. An electrical signal produced by the sensor(s) representative of sounds or vibrations produced by the heart or blood is processed, which may include digital conversion, to derive acoustical signal parameters, such as amplitude content, frequency content, relative time intervals, or the like as derived by acoustical sensing module 12 and/or control processor 16.

EGM sensing circuitry 14, coupled to at least one sensing electrode pair included in electrodes 13, is provided to sense cardiac signals, e.g. P-wave and/or R-wave signals attendant to the depolarization of the atria and ventricles of the heart, respectfully. EGM sensing circuitry 14 is coupled to electrodes 13, which may include transvenous intracardiac electrodes or epicardial electrodes for sensing cardiac EGM signals. In alternative embodiments, cardiac electrical signals may be sensed using subcutaneous or submuscular electrodes for sensing ECG signals. ECG signals and EGM signals are referred to herein generally as "cardiac electrical signals". Electrodes 13 may correspond to the electrodes 140, 142, 144, 148, 150 162 and 166 shown in FIG. 1 but may include fewer or more electrodes positioned in operative relation to one or more heart chambers. Cardiac electrical signals may be used for timing sensing windows used by acoustical sensing module 12 for obtaining acoustical signals. Cardiac electrical signals may additionally or alternatively be used by control processor 16 for timing therapy delivery, such as electrical stimulation pulses during CRT or other pacing therapy, e.g. according to programmed pacing intervals, such as a programmed atrial-ventricular (AV) interval and/or inter-ventricular (VV) interval.

Therapy delivery module 15 is provided for delivering pacing pulses to the patient's heart via electrodes 13 using programmable pacing parameters. Electrodes 13 used for delivering pacing pulses may include dedicated pacing electrodes, or may include shared pacing and sensing electrodes. Switching circuitry may be included in therapy delivery module 15 and sensing module 14 for selecting which electrodes 13 are coupled to EGM sensing circuitry 14 and which electrodes are coupled to therapy delivery module 15 as well as the polarity of such electrodes. While two electrodes are shown coupled to therapy delivery module 15 and two electrodes are shown coupled to EGM sensing module 14 in FIG. 2, it is recognized that multiple sensing and pacing channels corresponding to multiple heart chambers may require multiple electrodes coupled to each of sensing module 14 and therapy delivery module 15 and such connections may be controlled by a switching circuit.

Therapy delivery module 15 is controlled by control processor 16 to deliver pacing pulses according to a therapy delivery algorithm. Control processor 16 receives signals from EGM sensing circuitry 14 for use in controlling therapy delivery module 15 to deliver appropriately timed pacing pulses and/or cardioversion/defibrillation shock pulses. In other embodiments, neurostimulation may be delivered. In still other embodiments, therapy delivery module may include a fluid pump for delivering a drug for treating a detected condition. As will be described herein, an automatically delivered therapy may be started, stopped or adjusted by control processor 16 in response to parameters derived from acoustical signals.

Control processor 16 may include any one or more of a microprocessor, a digital state machine, a digital signal processor (DSP), an application specific integrated circuit (ASIC), a field-programmable gate array (FPGA), or equivalent discrete or integrated logic circuitry. In some examples, processor 16 may include multiple components, such as any combination of one or more microprocessors, one or more controllers, one or more DSPs, one or more ASICs, or one or more FPGAs, as well as other discrete or integrated logic circuitry. The functions attributed to control processor 16 herein may be embodied as software, firmware, hardware or any combination thereof, implemented in a single device or distributed across two or more devices, which may include one or more implantable devices, external devices, or a combination of both.

Control processor 16 includes an acoustical signal analysis module 22 for analyzing acoustical signals obtained by sensing module 12. The analysis module 22 includes circuitry and/or computer-readable instructions for performing an algorithm for deriving parameters and/or trends or relative changes in parameters derived from the acoustical signals.

Memory 18 stores algorithms used by control processor 16 for performing monitoring procedures. Such algorithms may include monitoring protocols for acquiring acoustical signals as well as controlling therapy response and/or triggering patient or clinician alert generation. Memory 18 may also be used to store other data and information used by control processor 16 for controlling device functions, including a pacing or neurostimulation therapy delivered by therapy delivery module 15, controlling sensing functions by EGM sensing circuitry 14, controlling telemetry module 20, and controlling patient alert 24 in response to detecting an alert condition based on acoustical signals and cardiac electrical signals. Alerts or notifications may be triggered by control processor 16 in response to acoustical signal measurements and transmitted to an external programmer via telemetry 20. Alternatively or additionally, a patient alert module 24 may generate audible sounds, a vibration, electrical stimulation to cause muscle twitching, or other alert signal perceivable by the patient.

Memory 18 may include computer-readable instructions that, when executed by processor 16, cause IMD 10 and processor 16 to perform various functions attributed throughout this disclosure to IMD 10 and processor 16. The computer-readable instructions may be encoded within memory 18. Memory 18 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

It is contemplated that IMD 10 may include or be coupled to other sensors 28 which provide signals to control processor 16 correlated to other physiological conditions of the patient. Sensors 28 may include an activity sensor, posture sensor, pressure sensor, oxygen sensor, temperature sensor, impedance sensor or the like. Sensor signals may be used by control processor 16 in detecting a physiological condition of the patient indicating a need to provide or adjust therapy or generate a patient alert.

Telemetry module 20 is configured for bidirectional communication with an external programmer 170 or computer operating software for programming the IMD 10. Control processor 16 may generate acoustical data and information relating to a monitored condition that is transmitted to an external device via telemetry module 20 for review by a clinician. In some embodiments, functions attributed herein to control processor 16 may be performed across one or more processors that may include an external processor receiving data from telemetry module 20, such as processor 174 of external programmer 170.

Figure 3A:
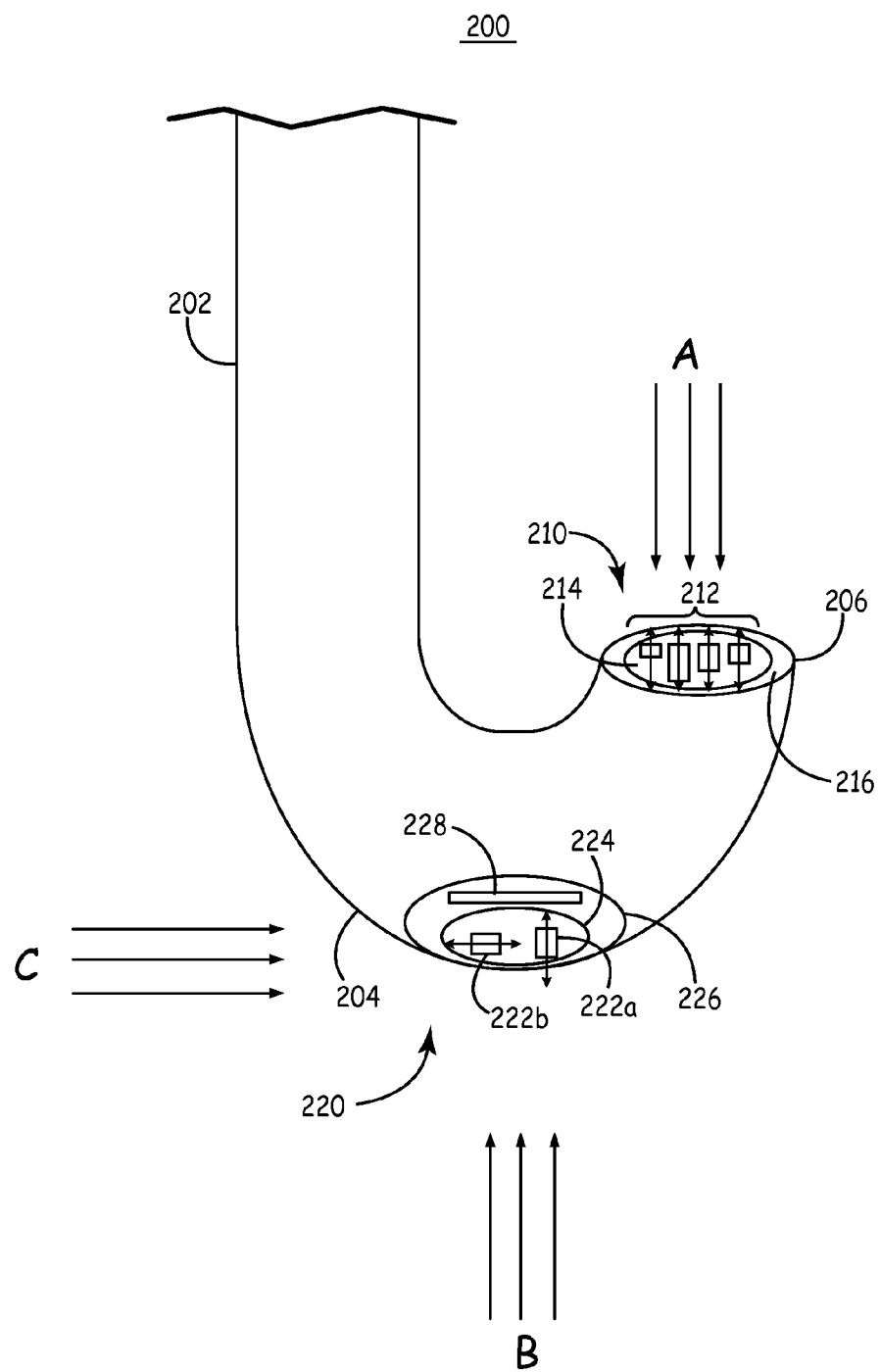
FIG. 3A is a view of a distal portion of an acoustical sensing lead incorporating a hydrophone according to one embodiment.

FIG. 3A is a view of a distal portion of an acoustical sensing lead 200 incorporating a hydrophone according to one embodiment. Lead 200 includes an elongated lead body 202 having a curve or bend 204 imposing a substantially "J"-shaped distal portion of the lead body 202. A pre-formed shape or curve of lead body 202 can provide a desired directionality of a hydrophone for "listening" to targeted cardiac sounds or blood flow at particular cardiovascular locations. For example, lead 200 is shown including two hydrophones 210 and 220. Hydrophone 210 is positioned at the distal lead end 206 which can be positioned for receiving sounds from a particular direction corresponding to sound source A due to the J-shape.

A second hydrophone 220 may be positioned along an outer diameter of a curve 220 to enable hydrophone 220 to receive sounds primarily from a different direction(s) than hydrophone 210. The hydrophones 210 and 220 may be oriented to receive acoustical signals from approximately opposite directions, for example from source A and source B, respectively. In various embodiments, one or more hydrophones may be carried by a preformed lead body having a particular shape designed to orient the hydrophone(s) for receiving sounds from specific directions for acoustical sensing from one or more targeted sources.

Hydrophone 210 includes a hermetically-sealed housing 216. A thin diaphragm or membrane 214 extends along an exposed portion of housing 216 and an array of acoustical transducers 212 are positioned along the diaphragm 214 within the housing 216. The exposed portion of housing 216 may be substantially flat or having a concave, conical or spherical surface to facilitate directional sensing of acoustical signals. The housing 216 may include a radio-opaque material such that the direction that the sensor 210 is facing relative to a patient's cardiovascular anatomy may be determined under fluoroscopy or x-ray.

Similarly, sensor 220 includes a housing 226 mounted within lead body 202 and enclosing acoustical transducers 222a and 222b (collectively "222"). A thin diaphragm or membrane 224 extends over acoustical transducers 222, such that transducers 222 are hermetically sealed within lead body 202. Sensor 220 is shown to include a reference mark 228 which may be provided as radio-opaque material along housing 226 for indicating the directionality of sensor 220 during an implantation or re-positioning procedure.

Acoustic transducer arrays 212 and 222 are embodied as piezoceramic transducers in one embodiment. The arrays 212 and 222 include two or more transducers of different sizes or other differing properties for providing sensitivity at different selected frequencies. The piezoceramic transducers may range from one to several millimeters in size to obtain signals responsive to a narrow band of frequencies from an overall range of sound frequencies from 10 Hz to 10 kHz. Along diaphragm 214, piezoceramic materials (or films) each having different frequency responses can be packed parallel to sense different sound frequencies. For example, individual transducers may be built to have different frequency ranges of 10-100 Hz, 100-1000 Hz, 1000-10 KHz and so on.

In alternative embodiments, the acoustic transducers may include a membrane capsule transducer or iridium tin oxide (ITO). Individual ITO transducers included in an array of transducers may range from tens of micrometers to one millimeter in width with a thickness of 100 nm to 1000 nm for obtaining different sound frequencies. The transducer arrays 212 is depicted in a linear arrangement in FIG. 3A, but may alternatively be arranged circumferentially or in other patterns relative to one another.

By placing multiple transducers responsive to different resonant frequencies within a hydrophone, different aspects of blood flow, blood pressure, and cardiac function such as wall motion and relaxation or valve closure and opening, may be monitored using sounds received from a targeted direction and in a targeted frequency range. For example, different frequency components of sound due to valve opening and closure may be examined to detect a change in blood pressure or cardiac function. Changes in power of the acoustical signal in different frequency ranges may be indicative of a change in blood flow pattern due to a change in a cardiac condition.

One or more piezoelectric transducers included in an acoustical sensor may be positioned within the sensor with its piezoelectric axis aligned in parallel with a direction of targeted sound source. In one embodiment, each of the transducers 212 is arranged with its piezoelectric axis aligned with or parallel to a direction of targeted sound source A, as indicated by the arrows extending through transducers 212. The transducers 212 will be less sensitive or insensitive to sounds arriving from directions that are not parallel to the aligned piezoelectric axes of the transducers 212.

In alternative embodiments, as shown by way of example in sensor 220, multiple transducers may be positioned within the sensor with associated piezoelectric axes aligned in different directions. Transducer 222a is positioned with its piezoelectric axis oriented in a first direction, as indicated by the arrow extending through transducer 222a, and transducer 222b is positioned with its piezoelectric axis oriented in a second direction, as indicated by the arrow extending through transducer 222b, that is different than the first direction. Transducer 222a is positioned with its piezoelectric axis oriented in a direction that is substantially parallel to the direction of targeted sound source B. Transducer 222b is positioned with its associated piezoelectric axis substantially parallel to the direction of a different targeted sound source C. A given piezoelectric transducer will be less sensitive or insensitive to sounds arriving from a source that is in a direction from the transducer that is substantially orthogonal to the piezoelectric axis. As such, directional sensitivity of an acoustical sensor includes a selected orientation of a piezoelectric axis of one or more transducers in some embodiments.

Figure 3B:
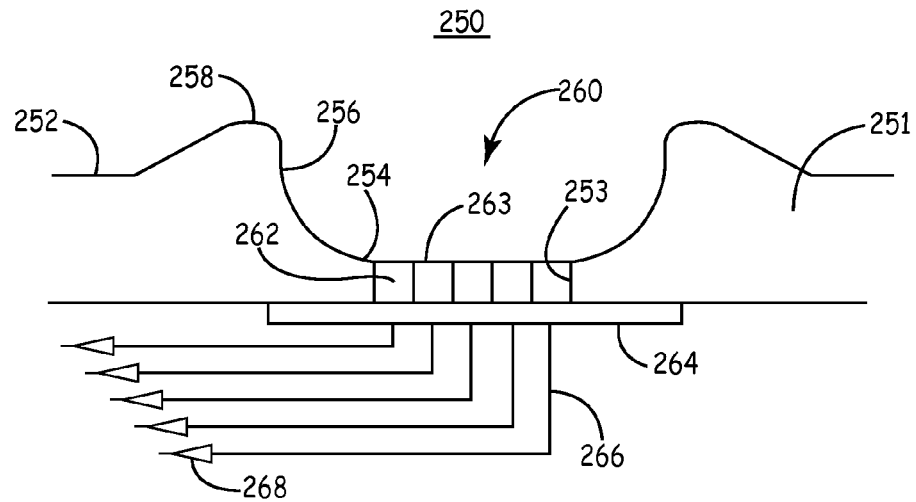
FIG. 3B is an enlarged sectional view of another example of a lead carrying a hydrophone for sensing cardiac and blood-flow related signals.

FIG. 3B is an enlarged sectional view of another example of a lead 250 carrying a hydrophone for sensing cardiac and blood-flow related signals. Lead 250 includes an elongated lead body 251 having an outer side 252. A hydrophone 260, which may include multiple transducers 262 responsive to distinct frequency ranges, is fixed along an opening 253 along an outer side 252 of the lead body 251. The opening 254 is shown formed along a recessed surface 254 of outer side 252, extending between a side wall 256. A raised flange 258 may surround the recessed surface 254, raising the height of side wall 256. The outer surface 263 of hydrophone 260 is hermetically sealed by a thin, biocompatible membrane or coating. In various embodiments, a thin film or coating of polyurethane, polytetrafluoroethylene (PTFE), silicone medical adhesive, or other blood compatible coatings or layers, which may include a bioactive layer or a layer that promotes cellular overgrowth, such as endothelial cell overgrowth may be applied over outer surface 263.

Transducers 262 are mounted along a hybrid circuit board 264 or other substrate which enables fixation of hydrophone 260 along lead body 251 and electrical connection to individual conductors 266 electrically coupled to each of transducers 262. Hybrid circuit board 264 and/or conductors 266 may include filters and amplifiers 268 for filtering and amplification of each transducer signal according to distinct filtering and amplification properties selected for each distinct frequency range of the individual transducers 262.

Figure 3C:
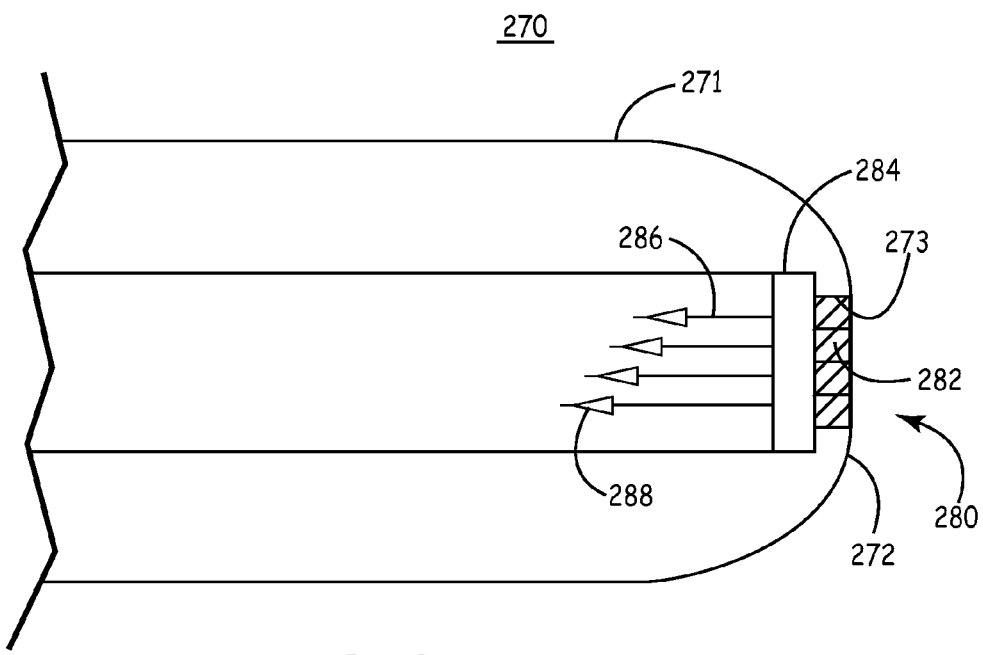
FIG. 3C is an enlarged sectional view of a distal tip of a lead carrying a hydrophone according to another embodiment.

FIG. 3C is an enlarged sectional view of a distal tip of a lead 270 according to another embodiment. Lead body 271 terminates at a distal tip 272 that is substantially spherical in shape, i.e. tip 272 is rounded forming a portion of a sphere. An opening 273 formed in the spherical tip 272 exposes one or more transducers 282 included in hydrophone 280. The exposed outer surface of hydrophone 280 is hermetically sealed along lead tip 272 by a coating or thin layer of a biocompatible material such as polyurethane or silicone as described above. As will be further described below, positioning a hydrophone along a recessed surface (as shown in FIG. 3B) or a rounded, conical or spherical surface of a lead body can provide greater directional sensitivity of the hydrophone.

The transducers 282 are mounted on a substrate 284, which may be a hybrid circuit board, which enables hydrophone 280 to be fixedly coupled within lead body 271 at distal tip 272. Transducers 282 are electrically coupled to individual conductors 286 via substrate 284 for carrying each transducer signal back to the acoustic sensing module 12 of the associated IMD. Each transducer 282 may be provided with unique filtering and amplification 288.

Figure 4A:
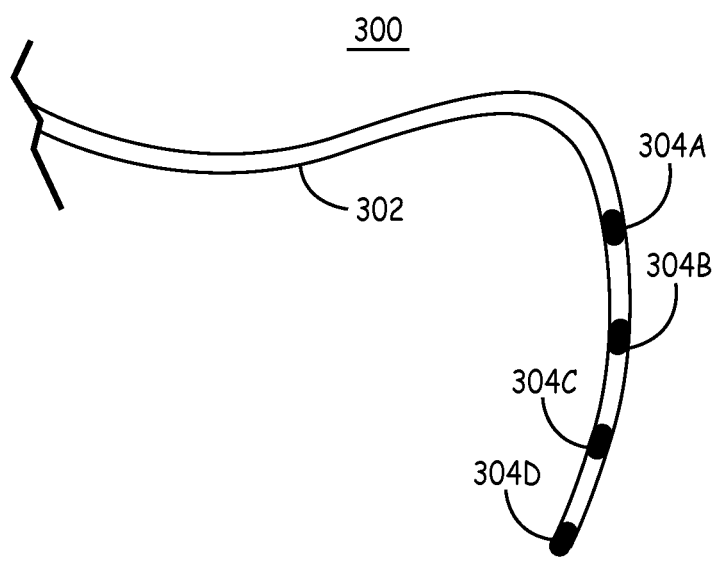
FIG. 4A is a schematic view of an acoustical sensing lead carrying multiple hydrophones according to one embodiment.

FIG. 4A is a schematic view of an acoustical sensing lead 300 according to one embodiment. Lead 300 includes an elongated lead body 302 carrying multiple hydrophones 304A through 304D. Each hydrophone may include one or more transducers to provide acoustical sensitivity in multiple frequency ranges. Each hydrophone 304A-304D may be positioned for sensing acoustical signals from a particular direction at different anatomical locations. For example, hydrophones 304A-304D may be spaced along lead body 302 such that when lead 300 is deployed along a blood vessel or the heart, each hydrophone 304A-304D is positioned at a particular level and location along a heart chamber or blood vessel to receive sounds from a targeted location.

In one embodiment, lead 300 is provided as a coronary sinus lead adapted for advancement through the coronary sinus and along a cardiac vein for positioning hydrophones 304A-304D at different locations along the patient's heart. Hydrophones 304A-304D can be positioned at different levels along the heart, e.g. along the left atrium, the mitral valve, the aortic valve, or the left lateral free wall along a mid-portion of the left ventricle. By providing multiple hydrophones having directional sensitivity, each having multiple transducers for specific sensitivity in multiple frequency ranges, a large amount of acoustical data specific to particular locations and blood flow phenomenon or cardiac motion can be obtained for monitoring cardiac function.

Openings along lead body 302 through which hydrophones 304A-304D receive sound waves may be defined in different directions for each of hydrophones 304A-304D to provide directional sensitivity of each hydrophone. For example, one hydrophone may be directed toward the aortic valve and one hydrophone may be directed toward the mitral valve. In one embodiment, a J-shaped lead as shown in FIG. 3 may be positioned in the right ventricle to direct a hydrophone for receiving signals from the direction of the mitral valve and a coronary sinus lead having multiple hydrophones may be positioned along a cardiac vein to direct at least one hydrophone in the direction of the aortic valve. In another embodiment, a lead in the right ventricle may carry a hydrophone directed toward the pulmonary valve and a coronary sinus lead may carry a hydrophone directed toward the aortic valve. Collection of directionally sensitive acoustical signals allows changes in opening and closing times between the two valves to be closely monitored.

A lead carrying a hydrophone may additionally carry other sensors or electrodes allowing multiple physiological signals to be acquired using the same lead. For example, a lead may carry electrodes for sensing cardiac EGM signals in addition to sensing acoustical signals to enable analysis of correlation between electrical cardiac activity and mechanical cardiac activity.

Figure 4B:
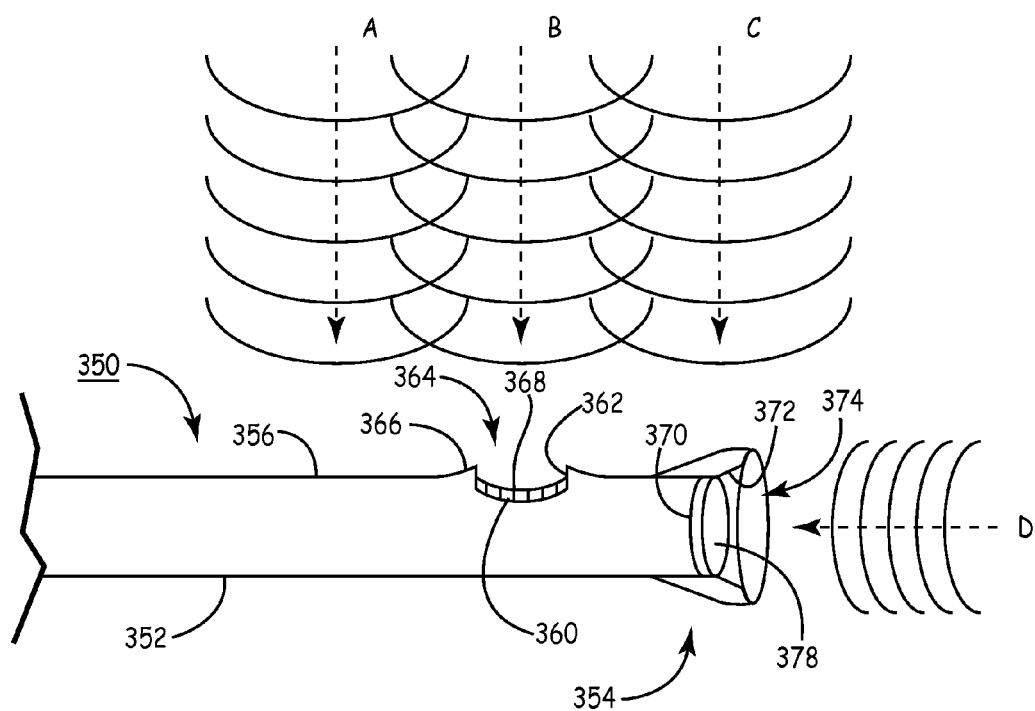
FIG. 4B is a schematic illustration of a lead carrying hydrophones for directional sensing of cardiac and blood flow related sounds.

FIG. 4B is a schematic illustration of a lead 350 carrying hydrophones for directional sensing of cardiac and blood flow related sounds. Lead 350 is shown carrying two hydrophone sensors 368 and 378, which may each respectively include one or more transducers designed to sense different frequency ranges. Lead 350 includes an elongated lead body 352 having a distal end 354 and outer side 356. Outer side 356 includes a recessed surface 360 surrounded by a sidewall 362. Sidewall 362 may extend in a generally circular, oval or rectangular shape around recessed surface 360. Recessed surface 360 and sidewall 362 promote directional sensitivity of hydrophone 368. Recessed surface 360 is shown to be concave in FIG. 4B, but may be substantially flat or convex in other embodiments.

Sidewall 362 extends from outer surface 356 to recessed surface 360. Lead body 350 may further include a raised lip, rim, or flange 366 along an edge of sidewall 362 defining opening 364. The protruding flange 366 extends sidewall 362 radially outward from outer side 356 and deflects sound waves not in approximate alignment with recessed surface 360. Sidewall 362 is shown to be substantially vertical, i.e. perpendicular to outer side 356. In other embodiments sidewall 362 may be angled with respect to outer side 356 and surface 360.

Hydrophone 368 will be more sensitive to sound waves generated by a source at location B than at A or C due to the recessed, concave surface 360 along which hydrophone 368 is mounted. Sound waves traveling directly from sources A and C toward lead body 352 will be reflected or obstructed by flange 366. Sound or vibrations reaching hydrophone 368 from sources not in approximate alignment with opening 364 and recessed surface 360 will be substantially diminished compared to a configuration in which hydrophone 368 is positioned along a non-recessed portion of outer side 356. In this way, a recessed surface 360 and sidewall 362 formed along an outer side 356 of lead body 350 promotes greater sensitivity of sounds produced by specific structures or at specific locations in the heart or blood vessels. In other examples, lead body 352 may be formed with multiple recessed surfaces formed at different radial and longitudinal locations along outer side 356 to hold hydrophones for receiving sounds from different preferential directions.

Hydrophone 378 is shown positioned at distal lead end 354 along a substantially flat recessed surface 370. Sidewall 372 defines a conical opening 374 through which hydrophone receives sounds from a preferential direction D. Sounds arriving from sources A, B and C will be deflected away from hydrophone 378. In this case, sidewall 372 is shown angled with respect to a substantially flat recessed surface 370. It is contemplated that in other embodiments, a hydrophone positioned at a distal lead end may be positioned along a concave or convex recessed surface extending between a substantially perpendicular or angled surrounding sidewall.

Figure 4C:
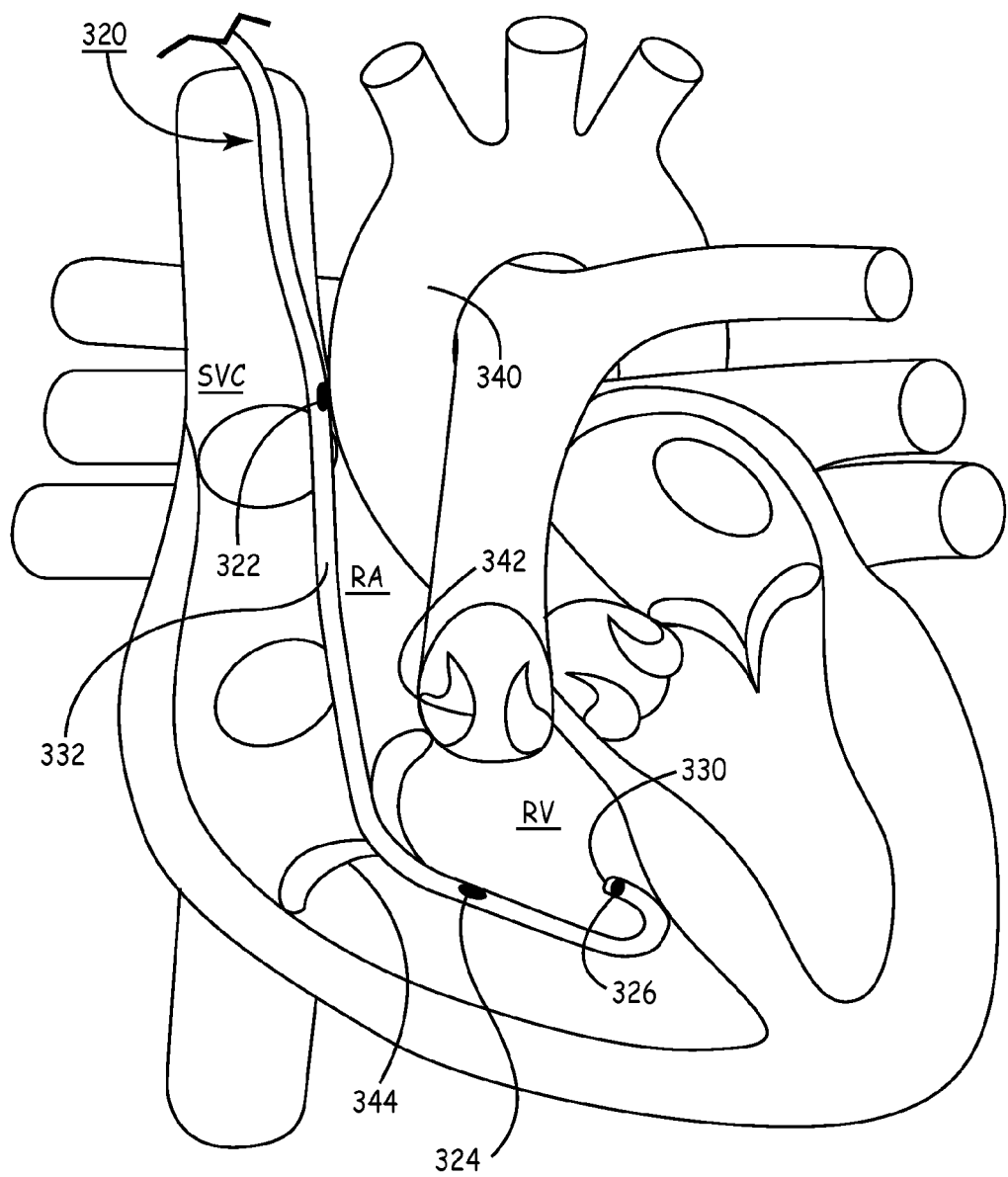
FIG. 4C is a cut-away view of a patient heart depicting an RV lead carrying hydrophones for directional sensing of heart and blood flow sounds.

FIG. 4C is a cut-away view of a patient heart depicting an RV lead 320 carrying hydrophones for directional sensing of heart and blood flow sounds. Lead 320 is a substantially J-shaped lead carrying a proximal hydrophone 322, a more distal hydrophone 324, and a distal tip hydrophone 326. Proximal hydrophone 322 and more distal hydrophone 324 are positioned along the outer side of the lead body 332, for example in a manner similar to sensor 368 shown in FIG. 4B. Distal tip hydrophone 326 is located in the distal tip of lead 320, for example in a manner similar to sensor 378 shown in FIG. 4B.

Proximal hydrophone 322 is located along an outer side of the lead body 332 such that it is positioned at the level of the superior vena cava (SVC) when the distal tip 330 is fully advanced into the RV. Positioned in the SVC, proximal hydrophone 322 can be directed toward the aorta 340 for receiving blood flow sounds in the aorta. As will be described below, blood flow sounds in the aorta may be analyzed to detect changes in blood flow velocity for use in detecting a cardiac condition. In alternative embodiments, a hydrophone may be positioned along the innominate vein for sensing blood flow sounds in the adjacent aorta.

Distal hydrophone 324 is positioned along the outer side of the lead body 332 such that it can be directed toward the pulmonary valve (PV) 342 when the lead distal tip 330 is fully advanced into the RV. Hydrophone 324 is positioned along the outer side corresponding to the inside curve of the "J" shaped bend of lead 320. Hydrophone 324 can be positioned to generate a signal with preferential sensitivity to pulmonary valve sounds and thereby generate a signal highly correlated to sounds produced by pulmonary valve opening and closure. When configured along a recessed surface of lead body 332 as described above, with or without a surrounding protruding flange, hydrophone 324 will be less sensitive to sounds or vibrations arriving from other structures such as the tricuspid valve 344.

Distal tip hydrophone 326 is located at the tip 330 of the J-shaped distal end of lead 320 such that it faces back toward the tricuspid valve 344 through which the lead 320 is advanced into the RV from the RA. Being within a recess of lead tip 330 surrounded by a sidewall as described in conjunction with FIG. 4b, hydrophone 326 will be preferentially sensitive to sounds produced by the opening and closure of the tricuspid valve 344 and less sensitive to sounds produced by other structures, such as the pulmonary valve 342.

This illustrative embodiment provides three hydrophones carried by a single lead body configured to preferentially sense acoustical signals from three different target sources, the aorta, the pulmonary valve and the tricuspid valve. It is recognized that numerous configurations and variations exist for deploying one or more hydrophones to particular locations, carried by one or more leads and each directed toward a preferential source of sound or vibration associated with cardiac function and blood flow.

It is recognized that lead 320 may be provided with one or more fixation members along lead body 320 to anchor the lead body at a desired location and to maintain a desired position and directional orientation of hydrophones 322, 324, and 326. For example, while not explicitly shown in FIG. 4C, a helical screw, hook or tine may be located along the curve of the J-shaped portion of the lead, at a distal end of the lead, or at proximal locations for anchoring the lead and respective hydrophones at desired locations.

Figure 5:
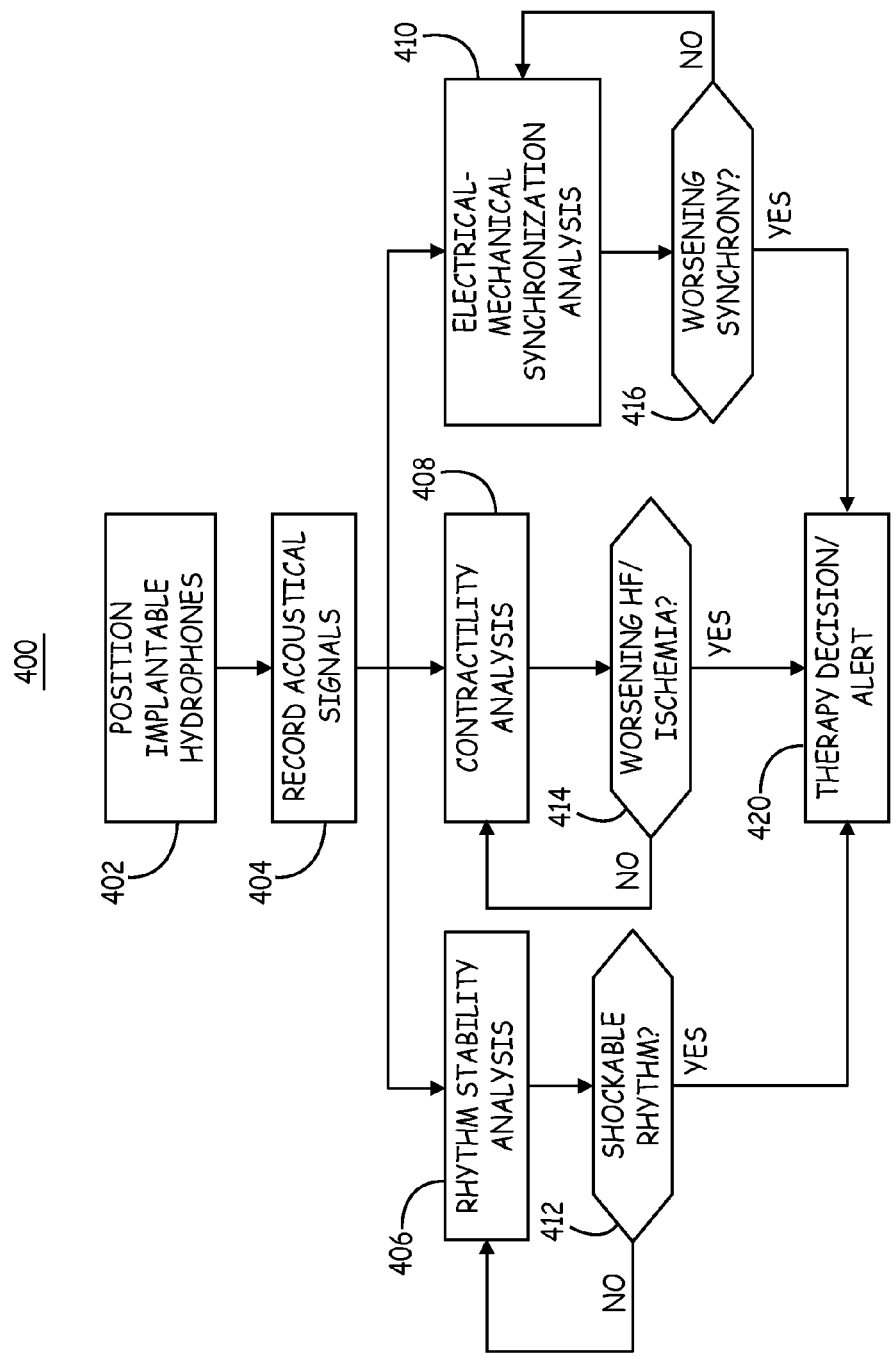
FIG. 5 is a flow chart of a method for monitoring cardiac function using an implantable medical device system including hydrophones.

FIG. 5 is a flow chart 400 of a method for monitoring cardiac function using an implantable medical device system including hydrophones. Flow chart 400 is intended to illustrate the functional operation of the device, and should not be construed as reflective of a specific form of software or hardware necessary to practice the methods described. It is believed that the particular form of software, firmware and hardware will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a non-transitory computer-readable medium that includes instructions for causing a programmable processor to carry out the methods described. A "non-transitory computer-readable medium" includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 402, multiple implantable hydrophones are implanted at desired locations for targeted acoustical sensing. In one embodiment, hydrophones are positioned for sensing mitral valve sounds, aortic valve sounds, tricuspid valve sounds, pulmonary valve sounds, LV free wall motion, and blood flow in the aorta or another major artery.

At block 404, acoustical signals from the positioned hydrophones are recorded. At blocks 406 through 410, analyses of the acoustical signals are performed to detect various cardiac conditions. At block 406, rhythm stability analysis is performed. Rhythm stability analysis is performed to detect a shockable rhythm at block 412. As further described below, rhythm stability analysis may include analysis of synchrony between electrical events and mechanical events and/or between mechanical events identified using signals received from the hydrophones.

A shockable rhythm is detected at block 412 based on fast electrical events and a low correlation between electrical and mechanical events or other changes in the hydrophone signals. Processor 16 makes a therapy decision and/or generates an alert at block 420. A cardioversion/defibrillation shock therapy may be delivered at block 420 in response to detecting a shockable rhythm based on signals received from the hydrophone(s). Additional details regarding using hydrophone signals for controlling a shock therapy are presented in conjunction with FIG. 6.

Contractility analysis is performed at block 408. Analysis to detect changes in myocardial contractility may include measuring the power and frequency content of a hydrophone signal(s) directed toward the pulmonary and/or aortic valves or mitral and tricuspid valves, the appearance of S3-related sounds, or changes in blood flow as detected by an increase in frequency components correlated to slow blood flow. As an example, a hydrophone may be advanced transvenously and placed directionally toward an artery extending adjacent to the vein. As described above, a hydrophone positioned in the superior vena cava or the innominate vein may be directed for preferential sensing of blood flow sounds in the aorta. The sound or vibration caused by blood flow in the artery is then sensed. In some embodiments, the sensor is placed near a bifurcation or an origin of an artery branch. The vibration or sound caused by blood flow will be correlated to the blood flow velocity or turbulence and/or blood pressure in the artery. Thus, by detecting and analyzing the characteristics of blood flow sound from an artery, a surrogate measure of blood flow velocity may be obtained.

Worsening myocardial contractility (block 414) may be responded to at block 420 by delivering a therapy and/or generating a patient or physician alert. A therapy delivered in response to worsening myocardial contractility may include cardiac pacing, neurostimulation, or drug delivery. Additional details regarding detecting worsening myocardial contractility are provided in conjunction with FIG. 8.

Electrical-mechanical synchronization analysis is performed at block 410 and may include analysis of acoustical signals from heart valves for determining synchrony between EGM events and valve-related sounds, synchrony between valves in left and right heart chambers and/or upper and lower heart chambers, changes in valve sounds signifying regurgitation, or appearance of an S3-related sound. If poor synchrony between the left and right sides of the patient's heart is detected as determined at block 416, a therapy response or alert is provided at block 420. In one embodiment, hydrophone signals are used for controlling cardiac resynchronization therapy (CRT) to improve cardiac chamber synchrony. Additional details relating to using hydrophone signals for detecting worsening synchrony and controlling CRT therapy are provided in conjunction with FIG. 7.

The analyses performed at blocks 406, 408 and 410 for detecting various cardiac conditions may be performed on a continuous basis or in response to detecting a change in another signal, such as an EGM signal. The analyses may be implemented singly or in any combination in an IMD.

Figure 6:
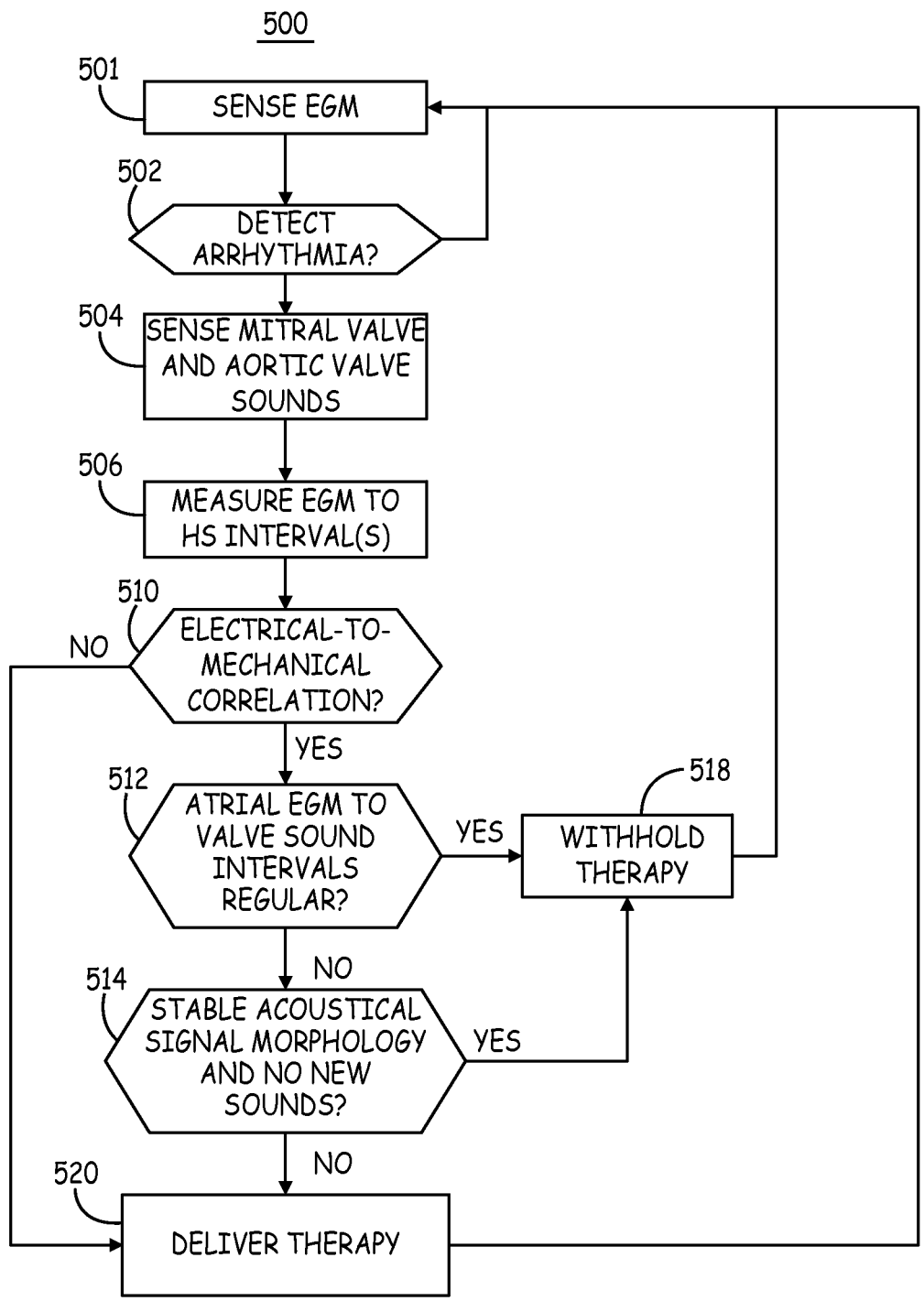
FIG. 6 is a flow chart of one method for using hydrophone signals for controlling shock therapy.

FIG. 6 is a flow chart 500 of one method for using hydrophone signals for controlling shock therapy. At block 502 an EGM signal is sensed from cardiac electrodes. Typically, the EGM signal (or an ECG signal) is a primary arrhythmia detection signal, monitored for initial detection of an arrhythmia. Initially, an arrhythmia is detected based on EGM signal monitoring, which may involve interval-based and/or morphology-based detection algorithms. When a preliminary arrhythmia detection is made based on EGM signal monitoring, hydrophones directed to receive signals specific to the mitral valve and the aortic valve are enabled at block 504 for providing acoustical signals to the IMD processing circuitry.

At block 504, hydrophone signals are received corresponding to the mitral valve and the aortic valve. The association between an event sensed on the EGM signal, such as an R-wave, and an event on the hydrophone signal is determined at block 506. Detecting association would include a 1:1 correspondence of the EGM and hydrophone signal events and occurrence of the events within an expected time interval range. Accordingly, time intervals between an EGM signal event and a hydrophone signal event are measured at block 506 to determine if there is electrical-to-mechanical correlation between these events at decision block 510. If not, the rhythm is detected as a shockable rhythm and cardioversion/defibrillation shock therapy is delivered at block 520.

If electrical and mechanical events are found to be correlated at block 510, time intervals between atrial EGM signals and valve-related sounds are measured at block 512. If there is correlation between atrial electrical activity, e.g. a P-wave, and valve sounds, the rhythm is determined to be a supraventricular rhythm and a cardioversion/defibrillation shock is withheld at block 518. If atrial EGM events are not associated with the aortic and mitral valve sounds at regular intervals, a ventricular arrhythmia is detected.

At block 514, the hydrophone signals are used to determine whether the ventricular arrhythmia is hemodynamically stable. The morphology of a hydrophone signal received from the direction of the aortic valve may be analyzed to determine if an expected signal morphology is present. The morphology analysis may include determining peak amplitudes and comparing the amplitude variability from beat-to-beat or comparing a peak amplitude to a threshold. Morphology analysis may include determining frequency content as sensed by multiple frequency range-specific transducers included in the hydrophone. If the frequency power spectrum changes significantly from an expected frequency power spectrum for normal sinus rhythm, hemodynamic instability may be detected. Baseline or threshold features of the hydrophone signals during normal sinus rhythm may be previously established and used for comparison at block 514.

High frequency signal components may provide blood flow information relating to changes in flow velocity, flow turbulence, valve regurgitation or other flow changes that an accelerometer or other acoustical sensors are insensitive to. Analysis of acoustical signals correlated to blood flow is not limited to signals arising from flow through a cardiac valve but may also include signals received by a hydrophone directed toward the aorta or other large artery or within a ventricular chamber.

Time intervals between the mitral valve signal events and the aortic valve signal events may also be examined at block 514. If stable acoustical signal morphology is found with no new sounds present, the ventricular tachycardia is detected as being hemodynamically stable. Shock therapy is withheld at block 518.

The process returns to block 501 and continues to acquire EGM and hydrophone signals until an arrhythmia is no longer detected or until the rhythm deteriorates to a hemodynamically unstable ventricular tachycardia as determined by the analyses performed at blocks 510, 512, and 514. If the acoustical signal morphology, frequency content, or associated time intervals are found to be unstable or if new sounds are detected, the ventricular tachycardia is determined to be a shockable rhythm, and a shock therapy is delivered at block 520. New sounds detected at block 514 may include sounds corresponding to S3 or S4 heart sounds.

Figure 7:
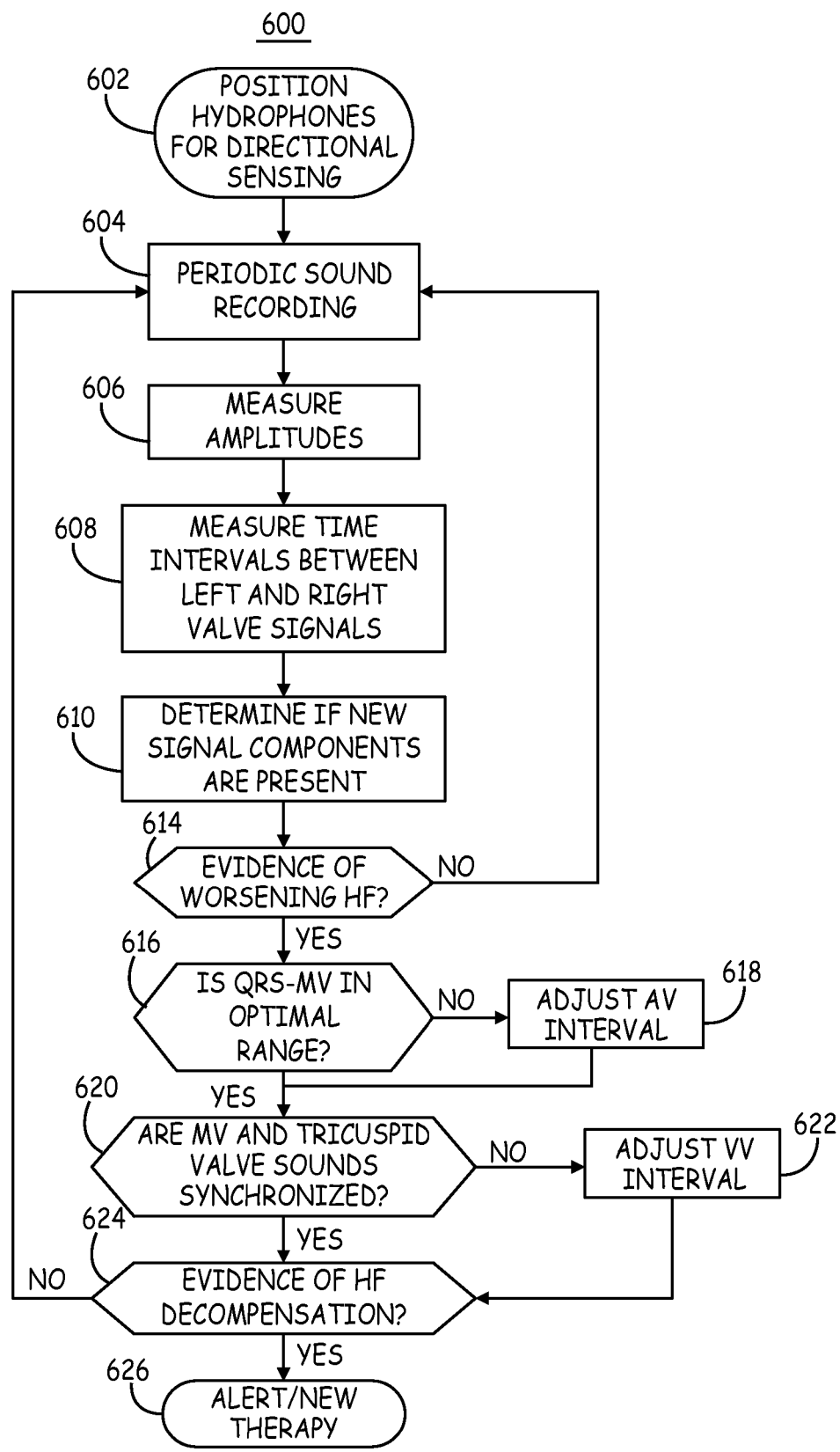
FIG. 7 is a flow chart of a method for monitoring heart failure using implantable hydrophones.

FIG. 7 is a flow chart 600 of a method for monitoring a heart failure condition using implantable hydrophones. Hydrophones carried by transvenous leads are positioned at targeted sensing locations at block 602 for directional sensing of specific arterial and cardiac sounds. Each hydrophone may include multiple transducers for sensitivity in individually specific frequency ranges. In one embodiment, one hydrophone is directed toward the mitral valve in the LV and another one toward the tricuspid valve in the RV. Additional hydrophones may be directed toward the aorta or pulmonary artery or another large artery, the aortic valve, the pulmonic valve, along the LV, along the RV or other desired monitoring locations. Methods described herein will relate to one hydrophone directed toward the mitral valve and one hydrophone directed to the tricuspid valve, however it is recognized that these methods may be expanded to include analysis of acoustical signals received by hydrophones directed to receive sounds from other cardiovascular locations.

At block 604, the hydrophone signals are recorded on a periodic basis, e.g. hourly, daily, weekly, monthly or other interval selected by a clinician. At block 606 through 612, the signals are analyzed to detect evidence of worsening HF or ventricular dyssynchrony.

At block 606, the amplitudes of the hydrophone signals are measured. Amplitude measurements may include determining a maximum or peak-to-peak amplitude from each transducer signal included in each hydrophone during a cardiac cycle or a portion thereof. As such, the sound intensity in multiple frequency ranges is measured for each hydrophone, i.e. for each directional sensing location. For example, the intensity of the mitral valve sounds in each of four frequency ranges and the intensity of the tricuspid valve sounds in each of four frequency ranges may be measured at block 606 from two hydrophones directed to preferentially receive mitral valve and tricuspid valve sounds, respectively. The number of frequency ranges monitored will depend on the number of transducers included in each hydrophone. All or a subset of available frequencies may be used for initial detection of a change in ventricular synchrony or HF status.

At block 608, time intervals between the left and right heart valve sounds are measured. For example, in a given frequency range, the time interval between a maximum signal peak in a mitral valve sound and a maximum signal peak in a tricuspid valve sound may be measured.

The appearance of any new acoustical signal components is determined at block 610. Occurrence of new sounds during time intervals not previously sensed may be an indication of a pathological change. For example, the appearance of sounds occurring during ventricular diastole relating to the S3 and S4 heart sounds may indicate a deteriorating heart failure condition. Increased signal intensity during time intervals or in frequency ranges not associated with normal acoustical signal intensity may indicate valve regurgitation, dilation of the heart, ventricular dyssynchrony, changing blood pressure or flow patterns, or other conditions associated with worsening heart failure. The appearance of new acoustical signal components, i.e. increased intensity of the acoustical signal, may be measured by measuring amplitudes or signal power for each of multiple frequency ranges and/or multiple time windows during the cardiac cycle.

At block 614, the measurements performed at block 606, 608 and 610 are used to detect evidence of worsening heart failure (HF). If decreased amplitudes compared to baseline acoustical signals, dysynchrony in measured time intervals, or new acoustical signal components compared to baseline acoustical signals are detected, evidence of worsening heart failure is detected. If no evidence of worsening HF is detected, the process returns to block 604 to continue periodic monitoring of the acoustical signals.

If worsening HF is detected, time intervals between a fiducial point of the EGM sensed QRS signal and an acoustical event associated with mitral and/or tricuspid valve closure are measured and compared to a predefined optimal time interval range or baseline at block 616. The time interval may be measured between an onset or peak of the QRS complex and an onset or peak of an S1 sound, for example. If the QRS-mitral valve (MV) time interval is outside an optimal time interval range, e.g. a threshold change from a previously established baseline measurement, the AV interval used to control CRT is adjusted at block 618. The AV interval may be adjusted until the QRS-MV time interval is within the optimal range, e.g. within a threshold range of the baseline measurement, or other optimization criteria may be used. An example of a threshold range that may be used is approximately ±20 ms.

After adjusting the AV interval or verifying that the QRS-MV interval is within a desired range, a time interval is measured between fiducial points of the acoustical signals received from the MV and from the tricuspid valve at block 620. If the time interval is within a predefined range, e.g. within a threshold range such as within of a previously established baseline measurement, indicating synchrony of the left and right heart chambers as determined at block 620, the process advances to block 624. Otherwise, the inter-ventricular (VV) timing interval used to control CRT pacing pulses is adjusted at block 622. The VV interval may be adjusted until fiducial points, such as a peak amplitude, of the MV and tricuspid valve signals are synchronized in one embodiment though other optimization criteria may be used. If the fiducial points of the two valve signals are within approximately 20 ms, the ventricles may be considered synchronized in one example.

After optimizing the AV and VV intervals if needed in response to the measured QRS-MV interval and the MV-tricuspid valve interval, the acoustical signals are examined for evidence of HF decompensation at block 624. After performing optimization of CRT, if evidence of HF decompensation remains, e.g., evidence of valve regurgitation, weakened (lower amplitude) or altered acoustical signal morphology, or presence of unexpected or abnormal acoustical signal components (in time or frequency domain), an alert may be generated at block 626 to notify the patient or clinician that medical attention may be warranted. Additionally or alternatively, a new therapy may be administered, which may involve neuromodulation using electrical stimulation or pharmacologic agents, or other automatic delivery of heart failure medication. The alert may notify the patient to take prescribed medications.

Figure 8:
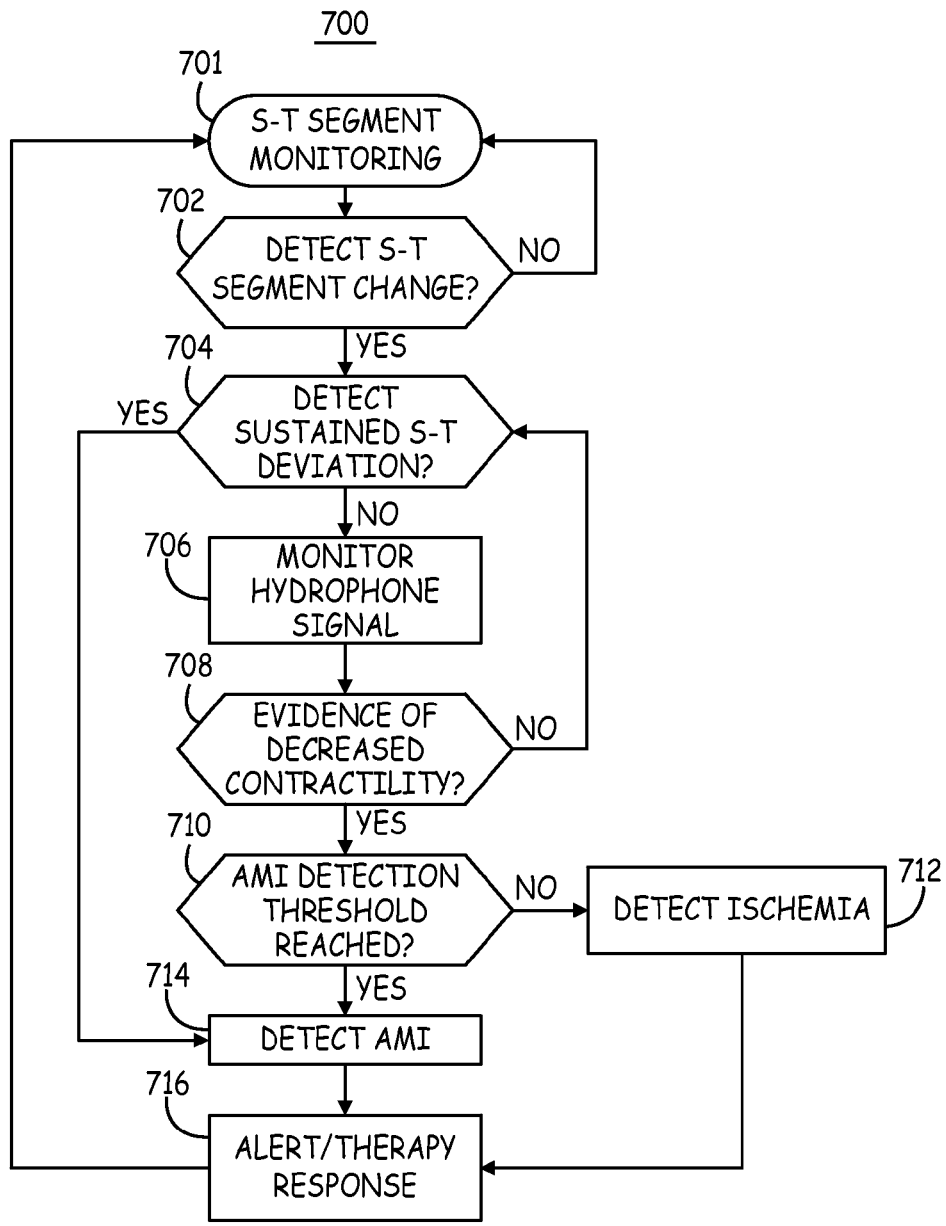
FIG. 8 is a flow chart of one method for detecting acute myocardial infarction (AMI) according to one embodiment.

FIG. 8 is a flow chart 700 of one method for detecting acute myocardial infarction (AMI) according to one embodiment.

Acoustical signals detected by hydrophones having specific orientations for directional sensing of cardiac sounds are used in conjunction with EGM (or ECG) signal monitoring for evidence of myocardial ischemia. At block 701, S-T segment monitoring of the EGM signal is performed. S-T segment deviation is an indication of myocardial ischemia. Detection of S-T segment changes at block 702 may be performed as generally disclosed in U.S. Pat. No. 6,937,899 B2 (Sheldon, et al.), hereby incorporated herein by reference in its entirety.

If a deviation in the S-T segment is sustained for a predetermined period of time or number of cardiac cycles, as determined at block 704, confirmation of AMI detection may be made at block 714. In some cases, however, the EGM signal analysis alone may not be conclusive. The S-T segment change may not reach a threshold change for a sustained period of time or the signal-to-noise ratio may preclude ischemia detection based on the EGM signal alone. If an S-T segment change is detected but EGM signal analysis is inconclusive in detecting AMI, one or more hydrophone signals are obtained at block 706.

In response to an S-T change that is either non-sustained or not reaching other threshold criteria, such as a threshold S-T elevation or depression, for detecting AMI, one or more hydrophone signals are monitored at block 706. Hydrophone signals are monitored for evidence of weakened contractility of the myocardium which may include altered flow patterns, valve regurgitation and increased intensity of diastolic sounds S3 and S4. Valve regurgitation sounds sensed primarily from the mitral or tricuspid valves are an indication of weak ventricular contraction during ischemia which causes weakened valve closure or dyssynchronous closures. In one embodiment, a hydrophone directed toward the mitral valve or aortic valve is used for sensing changes in valve sounds such as the appearance valve regurgitation, or changes in the amplitude, morphology or frequency content of mitral valve or aortic valve closure sounds. Since S3/S4 occurs during relaxation of ventricles and may be caused by free ventricular free wall vibration, a hydrophone may be directed to the LV free wall for sensing S3- or S4-related sounds.

If an S-T segment change is transient without correlation to compromised contractility based on heart sounds, as determined at block 708, the episode may be benign. The process may return to block 704 to continue to monitor for S-T segment deviation. If evidence of decreased contractility is detected from the hydrophone signals at block 708, measured changes in the hydrophone signal(s) may be compared to AMI detection thresholds at block 710. If intensity, frequency or morphology changes in the hydrophone signal(s) reach an AMI detection threshold, and/or changes in hydrophone signals are correlated in time with S-T segment changes, AMI is detected at block 714. Otherwise, the changes are attributed to myocardial ischemia at block 712. During AMI, either ST elevation or non-ST elevation AMI, the contractility will be compromised and this evidence can be obtained from the acoustical signals. During transient ischemia episodes, ischemia is typically short and not severe enough to compromise functionality. Thus transient or benign myocardial ischemia and AMI can be discriminated based on hydrophone signals.

Using one or more acoustic sensors, global versus local ischemia may be distinguishable as well as a general location of an infarct or ischemic area. For example, using multiple hydrophones having different directionality, the changes in acoustical signals may indicate the myocardial contraction is globally weak due to changes in multiple signals from multiple directions or only abnormal from a specific direction. EGM S-T segment deviation detected by an LV lead in conjunction with acoustical signal change associated with the mitral valve performance may indicate the ischemia/infarct location is in the LV free wall. EGM S-T segment deviation detected by an RV lead in conjunction with acoustical signal associated with tricuspid valve may indicate the ischemic/infarct location is in the RV. Identification of an area of suspected local ischemia may provide information regarding a location of coronary artery occlusion or stenosis and may be useful in guiding a therapy response and further diagnostic testing.

At block 716, an alert and/or therapy response is provided. If AMI is detected at block 714, an alert may be generated to notify the patient and clinician that immediate medical attention is warranted. A therapy may be adjusted, terminated or initiated in response to AMI detection. A therapy delivered in response to AMI detection may be a change to medication delivered by a drug pump, neuromodulation such as spinal cord stimulation for reducing sympathetic excitation, or a pacing therapy to reduce the heart rate. If myocardial ischemia is detected at block 712, a patient and/or clinician alert may be generated at block 716 and an automated therapy may be delivered. Automatic therapies delivered in response to myocardial ischemia may include those listed above for responding to AMI. In the case of transient myocardial ischemia, no therapy may be indicated. In some cases, a therapy response may include termination of a therapy. For example, if a pacing therapy has been delivered, it may be terminated until medical attention is provided or ischemia is no longer detected.

Figure 9:
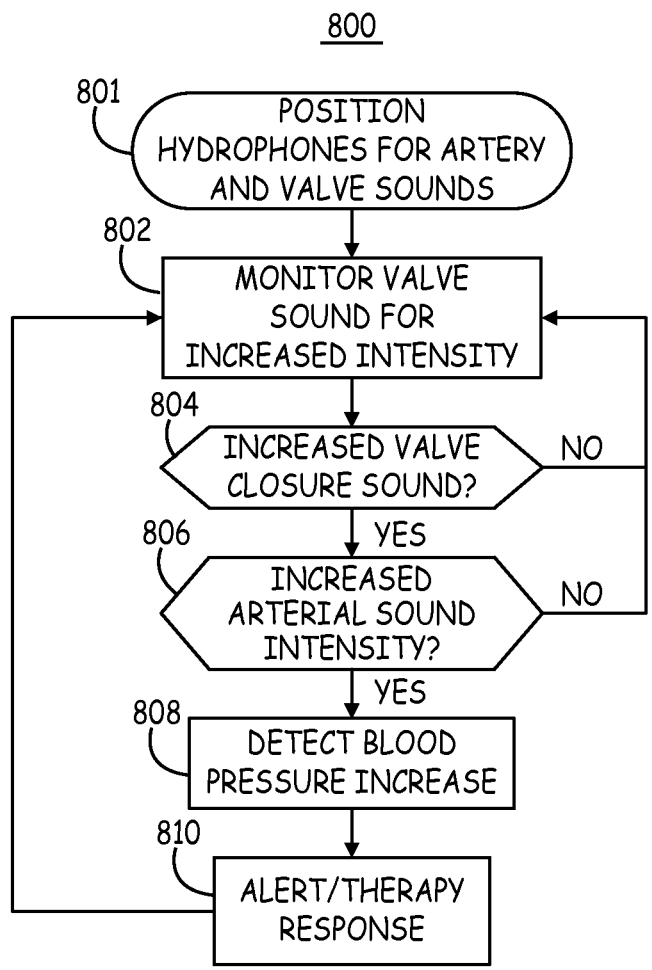
FIG. 9 is a flow chart of a method for monitoring for hypertension using hydrophone signals.

FIG. 9 is a flow chart 800 of a method for monitoring for hypertension using hydrophone signals. At block 801, one hydrophone is directionally positioned for receiving arterial sounds from an artery such as the pulmonary artery, aorta, or carotid artery. Typically the hydrophone will be placed transvenously with the hydrophone directed toward an artery for receiving a sound signal from an adjacent artery. For example, a hydrophone may be positioned in the left innominate vein and directed to receive acoustical signals from the aorta. A second hydrophone may be directionally positioned for receiving signals from a cardiac valve such as the aortic valve or the pulmonic valve.

At block 802, a signal from the hydrophone directed to the aortic or pulmonic valve is monitored. A particular narrow band frequency may be selected for sensing from one of multiple transducers included in the hydrophone to obtain a signal associated with the closure of the valve with high specificity and sensitivity. If an increase in intensity of the sound associated with valve closure is detected at block 804, e.g. compared to a baseline or predetermined threshold value, the arterial sound is monitored at block 806. In particular the arterial signal may be monitored during aortic or pulmonic valve closure. If the intensity of the arterial sound signal increases during valve closure, an increase in blood pressure is detected at block 808. Other aspects of the arterial signal may be monitored for detecting increased blood pressure, such as examining particular frequency components for evidence of increased blood flow velocity. Hydrophone signal frequency components may be correlated to blood flow velocity through calibration techniques at the time of manufacture. For example using a blood flow loop, hydrophone signal frequency content may be calibrated for varying flow velocities and pressures.

If an increase in blood pressure is detected, a patient or clinician alert and/or a therapy response may be provided at block 810. A therapy response to increased blood pressure may include neurostimulation to cause vasodilation or delivery of a vasodilator drug.

Thus, a medical device system and associated methods for acquiring and monitoring acoustical signals related to cardiac function have been presented in the foregoing description with reference to specific embodiments. It is understood that the various techniques and devices described may be implemented in any combination. It is appreciated that various modifications to the referenced embodiments may be made without departing from the scope of the disclosure as set forth in the following claims.

The invention claimed is:

1. A medical device, comprising:
a first elongated lead body having an outer surface and an opening along the outer surface;
a first sensor positioned along the lead body and configured to receive acoustic signals through the opening of the first lead body and generate an electrical signal representative of sounds produced at a targeted location along a patient's cardiovascular system;
a plurality of electrodes for sensing cardiac electrical signals;
a therapy delivery module for delivering a cardiac therapy via predetermined electrodes of the plurality of electrodes; and
a processor configured to:
detect a plurality of first cardiac events in response to the sensed cardiac electrical signals,
detect a plurality of second cardiac events in response to the acoustic signals;
determine a first plurality of time intervals between the plurality of first cardiac events and the plurality of second cardiac events,
determine a first correlation between the plurality of first cardiac events and the plurality of second cardiac events in response to the first plurality of time intervals,
responsive to the plurality of first cardiac events and the plurality of second cardiac events being correlated, detect a plurality of third cardiac events and a plurality of fourth cardiac events, wherein at least one of the plurality of third cardiac events and the plurality of fourth cardiac events are detected from the acoustic signals;
determine a second plurality of time intervals between the plurality of third cardiac events and the plurality of fourth cardiac events;
determine a second correlation between the plurality of third cardiac events and the plurality of fourth cardiac events in response to the second plurality of time intervals, and
control the therapy delivery module to deliver therapy in response to the determined second correlation.

2. The medical device of claim 1, wherein the first sensor comprises a hydrophone and the outer surface of the first lead body comprises a shaped contour for directing the opening for receiving the sounds from a direction of the first targeted location.

3. The medical device of claim 1, wherein the first sensor comprises a hydrophone and the cardiac electrical signals comprise atrial electrical signal events, and wherein the processor is configured to determine the second plurality of time intervals between the atrial electrical signal events and acoustic signal events, determine the second correlation between the atrial electrical signal events and the acoustic signal events, and control the therapy delivery module to withhold a tachyarrhythmia therapy in response to the determined second correlation.

4. The medical device of claim 1, further comprising:
a second elongated lead body having an outer surface and an opening along the outer surface; and
a second sensor positioned along the second lead body and configured to receive acoustic signals through the opening of the second lead body and generate an electrical signal representative of sounds produced at a second targeted location along a patient's cardiovascular system, wherein the first targeted location corresponds to a first heart chamber and the second targeted location corresponds to a second heart chamber different than the first heart chamber, and wherein the processor is configured to detect the plurality of second cardiac events in response to features of the acoustic signals from the first sensor and detect at least one of the plurality of third cardiac events and the plurality of the fourth cardiac events in response to features of the acoustic signals from the second sensor.

5. The medical device of claim 4, wherein the processor is further configured to determine the first plurality of time intervals between the first cardiac events detected from the cardiac electrical signal and the second cardiac events detected from acoustical signals from one of the first sensor and the second sensor, and, responsive to the determined first plurality of time intervals being outside a predetermined time interval range, adjusting a time interval controlling delivery of therapy via the therapy delivery module.

6. The medical device of claim 5, wherein the processor is further configured to
determine the second plurality of time intervals between the plurality of third cardiac events detected from the first sensor and the plurality of fourth cardiac events detected from the second sensor; and
responsive to the determined second plurality of time intervals being outside a predetermined time interval range, adjusting a time interval controlling delivery of therapy via the therapy delivery module.

7. The medical device of claim 1, wherein the outer surface of the lead body comprises a shaped contour for directing the opening for receiving the acoustic signals from a direction of the targeted location.

8. The medical device of claim 1, wherein the sensor comprises a hydrophone, the hydrophone comprising a plurality of transducers each responsive to a distinct sound frequency range and generating an electrical signal representative of sounds produced at the targeted location in the respective distinct sound frequency range.

9. The medical device of claim 8, wherein the plurality of transducers comprises a piezoelectric transducer having an associated piezoelectric axis, the axis aligned in a direction corresponding to an origination direction corresponding to the targeted location when the first lead body is positioned in the patient's body.

10. The medical device of claim 1, further comprising a second sensor positioned along the lead body and configured to receive acoustic signals, wherein the elongated body comprises:
a proximal end, a distal end, an outer side extending between the proximal end and the distal end, and a J-shaped bend near the distal end,
a first opening distal to the J-shaped bend of the elongated body;
a second opening along the outer side proximal to the J-shaped bend; and
at least one recessed surface along the outer surface of the lead body and one of the first opening and the second opening extending along the recessed surface, and wherein the first sensor is positioned along the first opening and the second sensor is positioned along the second opening.

11. A method for determining a cardiac condition in a medical device, comprising:
    positioning a first elongated lead body at a targeted location along a patient's cardiovascular system, the first elongated lead body comprising an outer surface and an opening along the outer surface and a first sensor positioned along the lead body and configured to receive acoustic signals through the opening of the first lead body;
    sensing cardiac electrical signals via a plurality of electrodes;
    detecting a plurality of first cardiac events in response to the sensed cardiac electrical signals;
    detecting a plurality of second cardiac events in response to the acoustic signals;
    determining a first plurality of time intervals between the plurality of first cardiac events and the plurality of second cardiac events;
    determining a first correlation between the plurality of first cardiac events and the plurality of second cardiac events in response to the first plurality of time intervals;
    responsive to the plurality of first cardiac events and the plurality of second cardiac events being correlated, detecting a plurality of third cardiac events and a plurality of fourth cardiac events, wherein at least one of the plurality of third cardiac events and the plurality of fourth cardiac events are detected from the acoustic signals;
    determining a second plurality of time intervals between the plurality of third cardiac events and the plurality of fourth cardiac events;
    determining a second correlation between the plurality of third cardiac events and the plurality of fourth cardiac events in response to the second plurality of time intervals, and
    controlling delivery of therapy by the device in response to the determined second correlation.

12. The method of claim 11, wherein the first sensor comprises a hydrophone and is positioned along a first targeted location, and the outer surface of the first lead body comprises a shaped contour for directing the opening for receiving the sounds from a direction of the first targeted location.

13. The method of claim 11, wherein the first sensor comprises a hydrophone and the cardiac electrical signals comprise atrial electrical signal events,
    wherein determining the second plurality of time intervals comprises determining time intervals between the atrial electrical signal events and acoustic signal events;
    determining the second correlation comprises determining a correlation between the atrial electrical signal events and the acoustic signal events; and
    controlling the delivery of therapy comprises withholding a tachyarrhythmia therapy in response to the determined second correlation.

14. The method of claim 11, further comprising:
    positioning a second elongated lead body at a second targeted location along a patient's cardiovascular system, the second elongated lead body comprising an outer surface and an opening along the outer surface and a second sensor positioned along the second lead body and configured to receive acoustic signals through the opening of the second lead body, wherein the first targeted location corresponds to a first heart chamber and the second targeted location corresponds to a second heart chamber different than the first heart chamber;
    detecting the plurality of second cardiac events in response to features of the acoustic signals from the first sensor; and
    detecting at least one of the plurality third cardiac events and the plurality of fourth cardiac events in response to features of the acoustic signals from the second sensor.

15. The method of claim 14, further comprising:
    determining the first plurality of time intervals between the plurality of first cardiac events from the cardiac electrical signals and the plurality of second cardiac events detected from acoustical signals from one of the first sensor and the second sensor; and
    responsive to the determined first plurality of time intervals being outside a predetermined time interval range, adjusting a time interval controlling delivery of therapy by the device.

16. The method of claim 15, further comprising:
    determining the second plurality of time intervals between the plurality of third cardiac events detected from the first sensor and the plurality of fourth cardiac events detected from the second sensor; and,
    responsive to the determined second plurality of time intervals being outside a predetermined time interval range, adjusting a time interval controlling delivery of therapy via the therapy delivery module.

17. The method of claim 11, wherein the outer surface of the lead body comprises a shaped contour for directing the opening for receiving the acoustic signals from a direction of the targeted location.

18. The method of claim 11, wherein the sensor comprises a hydrophone, the hydrophone comprising a plurality of transducers each responsive to a distinct sound frequency range and generating an electrical signal representative of sounds produced at the targeted location in the respective distinct sound frequency range.

19. The method of claim 18, wherein the plurality of transducers comprises a piezoelectric transducer having an associated piezoelectric axis, the axis aligned in a direction corresponding to an origination direction corresponding to the targeted location when the lead body is implanted in the patient's body.

20. A non-transitory computer readable medium having computer executable instructions for performing a method, the method comprising:
    positioning a first elongated lead body at a targeted location along a patient's cardiovascular system, the first elongated lead body comprising an outer surface and an opening along the outer surface and a first sensor positioned along the lead body and configured to receive acoustic signals through the opening of the first lead body;
    sensing cardiac electrical signals via a plurality of electrodes;
    detecting a plurality of first cardiac events in response to the sensed cardiac electrical signals;
    detecting a plurality of second cardiac events in response to the acoustic signals;
    determining a first plurality of time intervals between the plurality of first cardiac events and the plurality of second cardiac events;
    determining a first correlation between the plurality of first cardiac events and the plurality of second cardiac events in response to the first plurality of time intervals;
    responsive to the plurality of first cardiac events and the plurality of second cardiac events being correlated, detecting a plurality of third cardiac events and a plurality of fourth cardiac events, wherein at least one of the plurality of third cardiac events and the plurality of fourth cardiac events are detected from the acoustic signals;
determining a second plurality of time intervals between the plurality of third cardiac events and the plurality of fourth cardiac events;
determining a second correlation between the plurality of third cardiac events and the plurality of fourth cardiac events in response to the second plurality of time intervals, and
controlling delivery of therapy by the device in response to the determined second correlation.

* * * * *